United States Patent [19]

Bauer

[11] 4,390,621

[45] Jun. 28, 1983

[54] METHOD AND DEVICE FOR DETECTING GLUCOSE CONCENTRATION

[75] Inventor: Robert Bauer, Bristol, Ind.

[73] Assignee: Miles Laboratories, Inc., Elkhart, Ind.

[21] Appl. No.: 353,748

[22] Filed: Mar. 1, 1982

Related U.S. Application Data

[62] Division of Ser. No. 216,529, Dec. 15, 1980, Pat. No. 4,336,330.

[51] Int. Cl.³ .................. G01N 33/50; C12Q 1/54
[52] U.S. Cl. ......................................... 435/14; 422/56; 435/25; 435/28; 435/805; 435/810; 436/95
[58] Field of Search ............... 436/95; 435/14, 25, 435/28, 805, 810; 422/56, 57; 427/2, 3

[56] References Cited

U.S. PATENT DOCUMENTS

| | | | |
|---|---|---|---|
| 3,104,209 | 9/1963 | Scott | 435/14 |
| 3,798,004 | 3/1974 | Zerachia et al. | 422/56 |
| 3,964,871 | 6/1976 | Hochstrasser | 435/14 X |
| 4,211,845 | 7/1980 | Genshaw et al. | 252/408 X |
| 4,234,316 | 11/1980 | Hevey | 435/14 X |
| 4,247,297 | 1/1981 | Berti et al. | 436/95 X |
| 4,339,242 | 7/1982 | Magers et al. | 435/14 X |

FOREIGN PATENT DOCUMENTS

| | | | |
|---|---|---|---|
| 50-79392 | 6/1975 | Japan | 422/56 |
| 2045427 | 10/1980 | United Kingdom | 435/14 |

*Primary Examiner*—Kenneth M. Schor
*Attorney, Agent, or Firm*—James D. McNeil

[57] ABSTRACT

A method and test device for determining the glucose concentration in a test sample containing from ½ to 10 percent glucose are disclosed. The method and test device involve impregnating the carrier with an enzymatic testing composition which includes glucose oxidase, peroxidase and a chromogen. The carrier is subsequently impregnated with from 0.5 to 1.5 percent by weight polystyrene. Contact of the carrier with a glucose-containing test sample produces a detectable response whereby the glucose concentration can be determined.

7 Claims, 1 Drawing Figure

THE INFLUENCE OF
A POLYSTYRENE TREATMENT ON QUANTITATION

THE INFLUENCE OF
A POLYSTYRENE TREATMENT ON QUANTITATION

METHOD AND DEVICE FOR DETECTING GLUCOSE CONCENTRATION

This application is a division of application Ser. No. 216,529, filed Dec. 15, 1980, now U.S. Pat. No. 4,336,330.

BACKGROUND OF THE INVENTION

The detection of glucose in body fluids, as well as the determination of its concentration therein, is of great importance for diabetic patients who must control their diets so as to regulate their sugar intake and who must frequently be guided in this regard by a regular check on urine glucose. The determination of glucose in urine is also important where large numbers of people are screened to determine the incidence of diabetes among them.

Because early diagnosis and continued control are so important in diabetes, a glucose test, to be of greater value, must be conveniently rapid, simple enough for the technician or patient to learn with ease, accurate enough to serve the clinician or patient, sensitive enough to reflect variations in the patient's condition, and specific for glucose.

Currently there are available sophisticated biochemical systems which can be incorporated into dry, dip-and-read reagent strip devices, used in solution or suspension techniques, or in conjunction with spectrophotometics and other read-out systems.

These strips comprise a plastic strip, having at one end a carrier portion impregnated with an enzymatic testing composition which includes the enzymes glucose oxidase and peroxidase and one or more indicator compounds as the principal active ingredients. Buffering agents may be present to keep the pH of the reactants at the site of reaction at a predetermined pH range. The strip utilizes an enzyme system wherein the glucose is a substrate for glucose oxidase. Glucose is oxidized to gluconic acid with the concomitant formation of hydrogen peroxide. Indicator compounds present undergo color changes in the presence of hydrogen peroxide and peroxidase. Various indicators can be used including "benzidine-type" chromogens, e.g., benzidine, o-tolidine and tetramethylbenzidine and substituted aniline chromogens. A combination of indicators can be utilized.

The glucose enzymatic test strips referred to above enable the assay of glucose levels by measuring the rate of color change which the indicator undergoes, i.e., by a rate reaction. The sample to be analyzed for glucose is contacted with the reagent-incorporated carrier portion by momentarily immersing the carrier portion into the sample or by applying an aliquot of the sample to the carrier portion and measuring the response after a set period of reaction time, by comparing any color formed in the carrier portion with a standard color chart calibrated to various glucose concentrations.

The general principles of chemical reaction kinetics apply to enzyme-catalyzed reactions, but enzyme-catalyzed reactions also show a distinctive feature not usually observed in nonenzymatic reactions, saturation with substrate. The rate equation for reactions catalyzed by enzymes having a single substrate, e.g., glucose, is expressed by an equation known as the Michaelis-Menten equation. Under certain reaction conditions, the Michaelis-Menten equation can be used to derive a value known as the Michaelis-Menten constant ($K_M$) [See *Biochemistry*, Lehninger, 2nd Edition, pp. 189–192]. The equation expresses the mathematical relationship between the initial rate of the enzyme-catalyzed reaction and the concentration of the substrate. At high substrate concentrations, the $K_M$ of the glucose oxidase is exceeded and the reaction rate becomes nearly independently of concentration—this means that at such concentrations, it becomes difficult to determine concentrations of glucose based on a rate reaction color change. In the glucose-glucose oxidase system, as the level of glucose present approaches 2 percent, the $K_M$ of glucose oxidase is exceeded, rendering it difficult to determine with accuracy the glucose level of the sample being tested.

Diabetic patients can have glucose levels ranging from 50 mg/dl (0.05%) to 10,000 mg/dl (10%). Because of this wide range, for detection and treatment purposes, it is important to be able to quantitatively determine glucose levels in a range which encompasses about ½ up to 10 percent. At present, dip-and-read reagent strips do not enable determination of glucose levels which exceed about 2 percent.

The present invention overcomes this limitation of dip-and-read reagent strips and provides a method of measuring glucose levels of about ½ to about 10 percent.

SUMMARY OF THE INVENTION

The present invention is directed to an enzymatic method for determining the glucose concentration in a test sample containing from about ½ to 8 percent glucose. The method involves impregnating a carrier with an enzymatic testing composition which includes glucose oxidase, peroxidase and a chromogen and drying the impregnated carrier. The carrier is then impregnated with from 0.5 to 1.5 percent by weight polystyrene. The test sample is then contacted with the test device, a detectable response observed and the glucose concentration is determined. The device of the present invention comprises a carrier matrix impregnated with an enzymatic testing composition containing glucose oxidase, peroxidase and a chromogen and subsequently impregnated with from 0.5 to 1.5 percent by weight polystyrene.

DESCRIPTION OF THE PREFERRED EMBODIMENT

Figure 1:
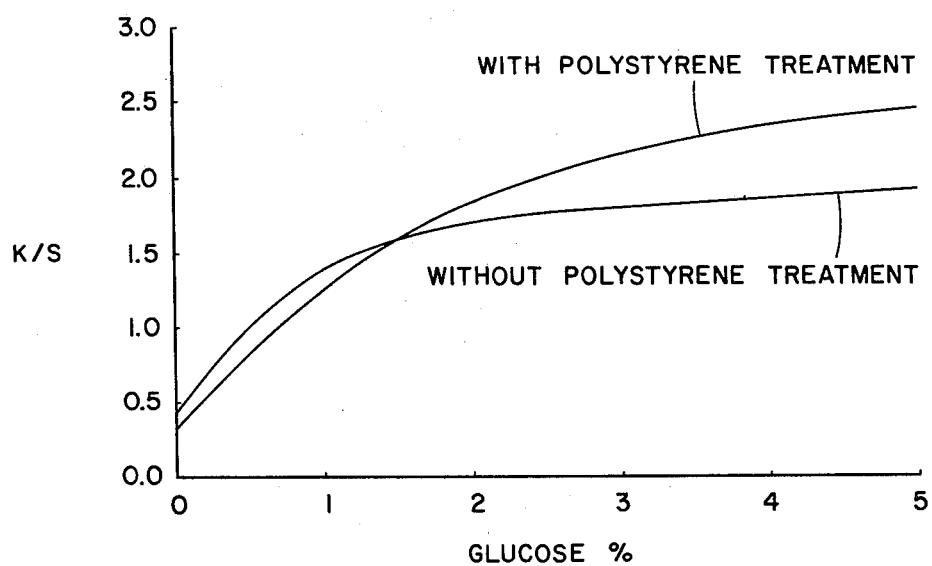

The carrier member used in the present invention can take on a multitude of forms. It can be mono- or multiphasic, comprising one or more appropriate materials or mediums of similar or different absorptive or other physical characteristics. It can be hydrophobic or hydrophilic, bibulous or nonporous. It can take on many known forms such as those utilized for enzymatic reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper carrier element. French Pat. No. 2,170,397 teaches the use of carrier members having greater than 50 percent polyamide fibers therein. Another approach to carrier members is disclosed in U.S. Pat. No. 4,046,513 wherein the concept of printing reagents onto a suitable carrier is employed. U.S. Pat. No. 4,046,514 discloses the interweaving or knitting of filaments bearing reagents in a reactant system. All such carrier member concepts can be employed in the present invention, as can others. Preferably the carrier member comprises a bibulous material, such as filter paper, whereby a solution or suspension of the glucose oxidase is used to impregnate the carrier member.

It may be desirable to utilize a multi-step application of reagents. In such a case, two or more solutions or suspensions of reagents are prepared, the carrier member being dipped substantially into each with drying steps between dippings. In such a case a porous material such as paper might be most advantageous. Alternatively, it might be desirable to utilize a multiphasic carrier member, where two or more layers of porous material are affixed one atop another. Still another approach to carrier member incorporation is to sequentially coat a continuous polymer with coatings containing different reagents of the immunoassay system. Filtering layers can be present in the carrier member to preclude potential interfering agents from reaching the assay system, while permitting access to any analyte present in the sample.

An indicated earlier, the carrier portion has incorporated therein glucose oxidase, peroxidase and an indicator, e.g., a "benzidine-type" chromogen or substituted aniline chromogen or a combination thereof. Optionally, one or more water soluble polymers may be incorporated, e.g., polyvinyl pyrrolidone and a nonionic surfactant, e.g., a polyethoxylated fatty alcohol to provide more uniform color during glucose testing. A suitable fatty alcohol sold under the trade designation Emulphor ON870, is available from GAF, New York, New York.

The carrier matrix can be impregnated with the enzymatic testing composition in several ways known to a person of reasonable skill in the art. One way is to pass a web of the carrier matrix material through an impregnating bath containing the testing composition ingredients so that the matrix becomes thoroughly saturated with impregnating solution. The saturated matrix is then dried, as in an air oven at 50° C., leaving the test composition incorporated within the matrix.

Subsequent to impregnating the carrier matrix with the enzymatic testing composition, the matrix is impregnated with a solution of polystyrene and dried. The range of polystyrene which produces improved determination of glucose levels is from about 0.5 percent to 1.5 percent (weight/volume). A preferred amount of polystyrene is about 1 percent.

The following Examples illustrate the determination of glucose concentration according to the present invention.

EXAMPLE 1

Commercially available Eaton and Dikeman 204 filter paper was dipped into an enzymatic testing solution having the following composition and dried for 15 minutes at 60° C.:

| | |
|---|---|
| Sodium citrate buffer, 1.0M, pH 5.5 | 4.0 ml |
| Horseradish peroxidase, 3 milligram/milliliter (mg/ml) | 4.0 ml |
| Glucose oxidase, 5000 U/ml | 0.06 ml |
| p-anisidine.HCl | 320.0 mg |
| Distilled water | 12.0 |

The filter paper was impregnated with a 1.0 percent solution (weight/volume) of polystyrene (molecular weight ~20,000) in toluene and again dried. Test strips were prepared from the treated filter paper and dipped into urine which contained glucose concentrations ranging from 0.0 to 5 percent. Control sample strips were prepared by impregnating untreated Eaton and Dikeman 204 filter paper with the above enzymatic testing composition, but without impregnating the paper with polystyrene.

The performance of the test strips prepared as described above was analyzed instrumentally using a device known as the "Rapid Scanner". This device is a scanning reflectance spectrophotometer interfaced with a PDP-12 computer obtained from the Digital Equipment Corporation. The instrument is used for the rapid measurement of reflectance spectra in the visual range. The computer allows for the storage of spectral data and computations. Measurements of the performances of test strips in the Rapid Scanner have the following advantages over visual observations.

1. The light source and conditions surrounding the sample remains fixed. In visual readings the light source can vary, not only in wavelength components, but also in relations to the locations of the strips being observed.

2. The detector characteristics remain fixed in the Rapid Scanner. In visual observation, the detector (i.e. in the eyes of the observer) varies from person to person and, with the same person, from day to day.

3. The Rapid Scanner allows more precise quantitation of the data than does human observation, thereby permitting comparisons between the results to be made in a more objective manner than with visual observation.

The Rapid Scanner instrument was constructed by the Ames Division of Miles Laboratories, Inc., Elkhart, Indiana, U.S.A., from whom complete information with respect to structural and performance characteristics is obtainable.

Reflectance values obtained at 540 nanometers (nm) wavelength, after a 60 second interval, are represented graphically in FIG. 1; where K/S is plotted against glucose concentration. K/S is defined as follows:

$$\frac{K}{S} = \frac{(1R)^2}{2R}$$

in which K is a constant, S is the scattering coefficient of the particular reflecting medium, and R is the fraction of reflectance from the test strip. This relationship is a simplified form of the well-known Kubelka-Munk equation [Gustav Kortüm, "Reflectance Spectroscopy", pp. 106-111, Springer-Verlaz, New York (1969)].

Slopes of segments of the K/S vs percent glucose carriers were calculated, assuming linearity for the segments. The slopes obtained are shown in Table 1 below.

TABLE 1

| | K/S vs. Glucose Slope Values | | |
|---|---|---|---|
| Glucose (%) | With Polystyrene | Without Polystyrene | $\left(\frac{\text{Percent without}}{\text{with}}\right) \times 100$ |
| 1.0-2.0 | 0.41 | 0.27 | 65.8 |
| 2.0-5.0 | 0.28 | 0.08 | 28.8 |

As seen in FIG. 1 and as calculated in Table 1, at glucose concentrations ranging from about ½ to about 5 percent, the polystyrene treated test strips have a greater slope than the untreated test strips. This greater slope indicates that in this glucose concentration range the reaction rate of the color change which occurs on the urea-formaldehyde treated carrier is still dependent upon the glucose concentration.

The untreated test strips have a lesser slope, i.e. are becoming more asymptotic at a faster rate in the range of about ½ to about 5 percent glucose concentration, indicating that the reaction rate of the color change which occurs on the untreated carrier is becoming more independent of glucose concentration, making it difficult to determine glucose concentration. The above example illustrates that the method of the present invention enables improved quantitation of the glucose concentration in a test sample within the range ½ to about 5 percent glucose.

As described below, another series of test strips was tested to determine the upper range of glucose concentration which can be measured according to the method of the present invention.

EXAMPLE 2

The commercially available filter paper described in Example 1 was dipped into an enzymatic testing solution having the following composition and dried for 15 minutes at 60° C.

| | |
|---|---|
| Sodium citrate buffer, 1.0M, pH 5.5 | 2.0 ml |
| Horseradish peroxidase, 3 mg/ml | 2.0 ml |
| Glucose oxidase, 5000 U/ml | 0.01 ml |
| p-anisidine.HCl | 400.0 mg |
| polyvinyl pyrrolidone (15%) | 2.0 ml |
| Emulphor 0N870 (5%) | 1.0 ml |
| Distilled water | 3.0 ml |

The filter paper was impregnated with a 1.0 percent solution (weight/volume) of polystyrene and the performance of the test strips analyzed as described in Example 1. Control sample strips were prepared as described in Example 1. K/S values were plotted against glucose concentration, and the slope of segments calculated, as summarized in Table 2 below.

TABLE 2

| K/S vs. Glucose Slope Values | | | |
|---|---|---|---|
| Glucose (%) | With Polystyrene | Without Polystyrene | $\left(\frac{\text{Percent without}}{\text{with}}\right) \times 100$ |
| 5.0–10.0 | 0.016 | 0.012 | 75.0 |

The results shown in Table 2 indicate that at glucose concentrations ranging from about 5 to 10 percent, the polystyrene treated test strips have a greater slope than the untreated test strips. The above test results, in conjunction with the test results shown in Example 1, indicate that the method of the present invention enables improved quantitation of the glucose concentration within the range ½ to about 10 percent glucose.

What is claimed is:

1. In a method for determining the glucose concentration in a test sample containing from about ½ to 10 percent glucose which method includes the steps of; contacting said sample with a test device which includes a carrier matrix impregnated with an enzymatic testing composition including glucose oxidase, peroxidase, and a chromogen; and observing a detectable response produced by said test device; the improvement which comprises impregnating the carrier matrix with a solution of from about 0.5 percent to 1.5 percent by weight of polystyrene subsequent to the impregnating of the carrier matrix with said testing composition.

2. A method as claimed in claim 1 wherein the carrier is paper.

3. A method as claimed in claim 1 wherein polystyrene is present in an amount of about 1.0 percent by weight.

4. A method as claimed in claim 1 wherein the chromogen is a benzidine-type indicator or a substituted aniline indicator.

5. A method for determining the glucose concentration in a test sample containing from about ½ to 10 percent glucose which comprises the steps of providing a test device which includes a carrier having inpregnated therein an enzymatic testing composition comprising glucose oxidase, peroxidase, and a chromogen; subsequently impregnating the carrier with from 0.5 percent to 1.5 percent by weight of a solution of polystyrene; contacting said test sample with the carrier of said test device; and observing a detectable response, whereby the glucose concentration is determined.

6. A method as claimed in claim 5 wherein the carrier is paper.

7. A method as claimed in claim 5 wherein the polystyrene is present in an amount of about 1.0 percent by weight.

* * * * *